United States Patent [19]

Lohmer et al.

[11] 4,069,052
[45] Jan. 17, 1978

[54] COLOR PHOTOGRAPHIC MATERIALS WITH SPIRO HETEROCYCLIC STABILIZING AGENTS COMPRISING 2-IMIDAZOLIDINE-4',5'-DIONE RINGS

[75] Inventors: Karl Lohmer; Anita von König, both of Leverkusen; Siegismund Schutz, Metzkausen; Jürgen Stoltefuss, Haan, all of Germany

[73] Assignee: AGFA-Gevaert Aktiengesellschaft, Leverkusen, Germany

[21] Appl. No.: 640,641

[22] Filed: Dec. 15, 1975

[30] Foreign Application Priority Data

Dec. 20, 1974 Germany .............................. 2460330

[51] Int. Cl.$^2$ ......................... G03C 1/48; G03C 1/34; G03C 7/00; G03C 1/40

[52] U.S. Cl. ........................................ 96/76 R; 96/56; 96/74; 96/77; 96/87 R; 96/100 R; 96/109; 427/299

[58] Field of Search ............... 96/109 R, 56, 77, 87 R, 96/100, 74, 76 R; 427/299

[56] References Cited

U.S. PATENT DOCUMENTS

| 3,137,578 | 6/1964 | De Selms | 96/109 |
|---|---|---|---|
| 3,582,333 | 6/1971 | Yost et al. | 96/109 |

*Primary Examiner*—David Klein
*Assistant Examiner*—Richard L. Schilling
*Attorney, Agent, or Firm*—Connolly and Hutz

[57] ABSTRACT

A photographic silver halide material containing a new stabilizer compound which is an aromatic compound containing in ortho position two bridging members which are linked to form a spiro structure with a 2'-imidazolidine-4',5'-dione as defined hereinafter.

7 Claims, No Drawings

COLOR PHOTOGRAPHIC MATERIALS WITH SPIRO HETEROCYCLIC STABILIZING AGENTS COMPRISING 2-IMIDAZOLIDINE-4',5'-DIONE RINGS

This invention relates to new stabilizing agents and their use in color photographic materials.

It is known to produce colored photographic images on recording materials which carry a red sensitive, a green sensitive and a blue sensitive silver halide emulsion layer on a support layer, each of the said silver halide emulsion layers usually containing non-diffusible color couplers for producing a cyan, magenta and yellow partial color image, each partial image being produced in the color which is complementary to the spectral sensitivity. Conventional color photographic materials also contain other layers, for example filter layers or antihalation layers, usually between the substrate and the lowermost silver halide emulsion layer, as well as additional gelatine intermediate layers or a covering layer.

It is becoming increasingly common in photographic practice to mount the layers on hydrophobic support layers, and various methods are known in the art to improve the bond between the hydrophilic photographic layers, which usually contain gelatine, and the substrate. For example, polyester foils or foils of polyolefines or polyolefine coated paper substrates are irradiated with electrons or exposed to a corona discharge. These methods have been described in British Pat. Nos. 971,058 and 1,060,526 and in U.S. Pat. No. 3,220,842.

Due to various influences in the photographic layers and/or the atmosphere the photographic materials shown often an increased tendency of production of fog and/or the sensitivity of one of the three emulsion layers is altered during the storage of the photographic material which could heavily reduce the image quality.

These unpredictable influences are especially pronounced in color photographic materials having hydrophobic substrates which are subjected to a corona discharge prior to the coating thereof with the photographic layers.

It is moreover well known that if color photographic silver halide emulsion layers are applied to electron irradiated hydrophobic substrates and this application is carried out soon after the irradiation, the emulsion layer next to the substrate is found to have an exceptionally heavy fog after it has been exposed and subjected to conventional color photographic processing, or it is found to have cloudy color patches in areas of uniform color density, presumably due to an uneven desensitization effect. According to U.S. Pat. No. 3,582,333, the fog produced by electron irradiation can be improved by conventional reducing agents, in particular polyhydroxybenzene and 3-pyrazolidone derivatives. Although these reducing agents in part have the desired stabilizing effect, they themselves are unable to remain stable in photographic casting solutions and layers for any length of time without the addition of antioxidants such as bisulphites because they are sensitive to oxidation. Since it is regarded a necessary requirement of photographic materials that they should be able to be stored for a considerable time without undergoing any change in their properties, these reducing agents are not satisfactory in practice, particularly since their oxidation products discolor the layers and, moreover, these stabilizing agents must be used in considerable concentrations to have the desired effect.

It is therefore an object of this invention to provide new stabilizing agents for color photographic materials. The stabilizing agent provided by the present invention is capable of substantially reducing color fog of the color photographic images of any kind of conventional color photographic materials.

It is a further object of the present invention to provide new stabilizing agents for color photographic materials having a hydrophobic support and in particular of color photographic materials which contain corona irradiated substrates.

It is a particular preferred embodiment of the present invention to provide stabilizing agents for the reduction of color fog and/or against alteration of sensitivity in emulsion layers in color photographic materials which emulsion layers were cast onto a corona irradiated or electron irradiated substrate more or less immediately after irradiation thereof.

The new stabilizing agents of the present invention are 2,2'-spiro-imidazolidine-4',5'-dione derivatives of o-substituted aryl compounds or more specifically defined phenyl compounds in which the phenyl ring is ortho disubstituted with two 6-electron bridging members, said members being linked together to form a spiro structure with 2'-imidazolidine-4', 5'-dione.

Examples of 6-electron bridging members are oxygen, sulfur and the group NH. They are belonging either to the main group VI of the periodic system and have 6 electrons in the outer shell or they belong to lower main groups of the periodic system and have hydrogen atoms attached to them so that the total number of the electrons of the outer shell of the said bridging member and the hydrogen atom is 6 (such as in NH as bridging member).

It is preferred to use spiro compounds in accordance with the present invention in which at least one of the bridging members carries no more than one hydrogen and in which at least one bridging member is oxygen or NH.

The said spiro compounds as specifically defined above substantially reduce the tendency of fogging in any kind of color photographic materials and are particularly advantageous if used in color photographic materials containing a hydrophobic substrate.

The reduction of fog can be observed in the first silver halide emulsion layer which is adjacent to the support as well as in the silver halide emulsion layers which are positioned onto the first silver halide layer. The layers may hereby be optionally separated by one or more intermediate layers and/or filter layers.

The above mentioned effect can also be observed in photographic materials having any kind of commonly known supports, and if the support used is a corona irradiated hydrophobic support, the effect can be observed even if the emulsion layers have been applied onto the support after having passed a long time after the corona irradiation of the substrate.

Furthermore it has been noted that color photgraphic material of the present invention containing 2,2'-spiro-imidazolidine-4', 5'-dione derivatives of o-substituted aryl compounds as stabilizing agents does not show any signs of increased fogging or patchiness or reduction in sensitivity after development if the silver halide emulsion layer is applied either directly or after an intermediate layer to the irradiated substrate more or less immediately after irradiation, that is to say within a period of one second to 30 minutes.

The particular preferred embodiment of the present invention therefore relates to a photographic material comprising a hydrophobic support which has been treated with a corona discharge current and has thereafter immediately been coated with at least one hydrophilic colloid layer which contains a silver halide emulsion and color couplers, the emulsion being applied directly to the substrate or after application of a hydrophilic intermediate layer, and the photographic material containing 2,2'-spiro-imidazolidine-4', 5'-dione derivatives of o-substituted aryl compounds as stabilizing agents in the emulsion layer or intermediate layer immediately adjacent to the substrate. After prolonged storage followed by exposure and color development with a conventional aromatic color developer containing primary amino groups, the material according to the invention shows neither unwanted fogging or patchiness nor regression in sensitivity, and the sensitometric characteristics of the color images obtained are in no way inferior to those obtained with materials in which the emulsion layers are not applied directly and immediately but only after a prolonged period of time to a conventional intermediate bonding layer.

Compounds of the following general formula are particularly suitable:

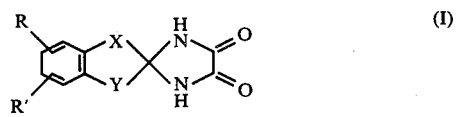
(I)

in which

R and R' which may be the same or different, represent hydrogen, an alkyl group preferably with 1 to 10 carbon atoms, more preferably with 5 to 10 carbon atoms, a cycloalkyl group such as cyclohexyl or cyclopentyl, an aryl group such as phenyl, an aralkyl group in particular a phenylalkyl group, the alkyl group having up to 4 carbon atoms such as benzyl or phenylethyl, or halogen such as chlorine or R and R' together represent the carbon atoms required to complete a condensed cyclohexene, cyclohexadiene or benzene ring, X represents oxygen or -NH- and Y represents oxygen, sulphur or -NH-.

It is expecially desirable for R or R' to be substituted para to either bridging member X and Y.

The heterocyclic spiro compounds of the above formula I are new and can easily be prepared in known manner by reacting cyanamide with oxalyl chloride as described e.g. in the Journal Chem. Ber. 103, 2006-2007 (1970) and then reacting the resulting 2,2-dichloro-imidazolidine-dione-(4,5) with a phenyl compound in which the phenyl ring is ortho disubstituted with two 6-electron bridging members carrying groups which are capable of reacting with the said 2,2-di-chloro-imidazolidine-dione-(4,5) to form the desired spiro structure.

Examples of those groups are hydroxy, methoxy amino and mercapto groups.

Especially suitable are compounds of the formula

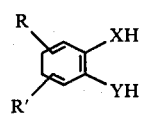
(II)

in which R, R', X and Y have the meanings specified above, in a one pot process without first isolating the 2,2-dichloroimidazolidine-dione-(4,5).

The following are examples of compounds which are suitable for the reaction: Pyrocatechol, 4-chloropyrocatechol, 4,5-dichloropyrocatechol, 3,4-dihydroxy-tert.-butyl-benzene, 3,4-dihydroxy-cyclohexyl-benzene, 3,4-dihydroxy-tert.-octyl-benzene, o-amino-phenol, o-amino-thiophenol and o-phenylenediamine.

When carrying out the process, anhydrous cyanamide and oxalyl chloride are mixed with stirring in a molar ratio of 1:1 in an inert, anhydrous organic solvent such as ether, benzene, methylene chloride or tetrahydrofuran, or, preferably, dioxane at a temperature of about 20° C. The new spiro compounds are obtained after addition of the compound of the above formula II in a 1- to 4-times molar quantity at a temperature of from 20° to 100° C, preferably 20° to 90° C. The reaction may be carried out with or without acid binding compounds such as triethylamine or pyridine. If X in the above formulae represents —NH—, the hydrogen chloride obtained can be bound by an excess quantity of compound of the above formula II.

The reaction products obtained either precipitate, in which case they can be suction filtered, or they are isolated in the usual manner by evaporation of the solvent. The crude product is purified by recrystallisation or reprecipitation from suitable solvents.

Examples of heterocyclic spiro compounds which may be used according to the invention are given below.

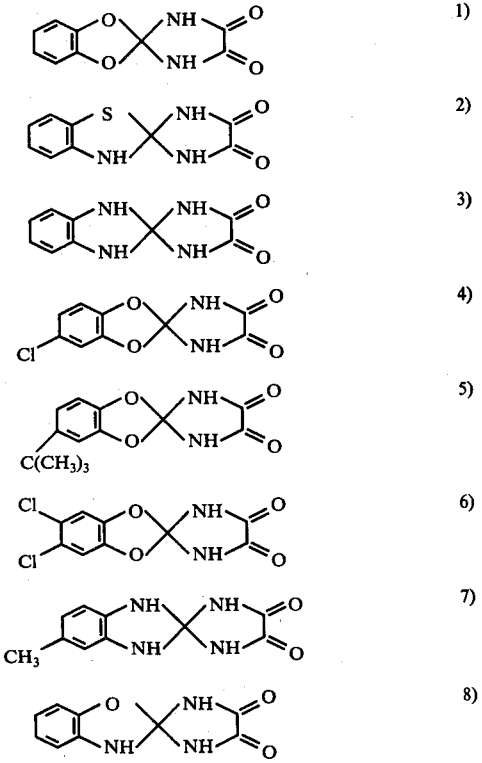

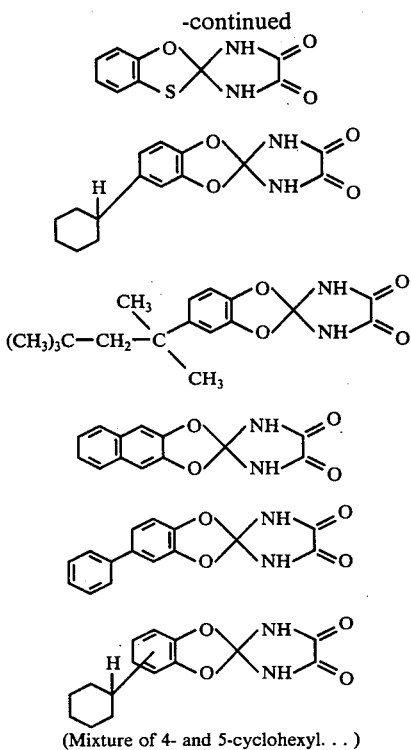

(Mixture of 4- and 5-cyclohexyl...)

The preparation of compounds according to the invention is described in detail below.

Example of Preparation 1

0.155 mol (6.5 g) of dehydrated cyanamide were put into 500 ml of anhydrous dioxane and 0.155 mol (19.65 g) of oxalyl chloride were added dropwise at 20° C. After 2 hours' stirring, 0.155 mol (17.1 g) of pyrocatechol, dissolved in 50 ml of dioxane, were added dropwise. The reaction mixture was stirred overnight, suction filtered to remove precipitate and washed with dioxane and water. The solid product was dried and stirred up with about 200 ml of acetone, filtered with Tonsil and evaporated to dryness under reduced pressure at a bath temperature of about 35° C. 13.2 g, which is 41.4% of the theoretical yield, of spiro-[1,3-benzodioxol-2,2'-imidazolidine]-4',5'-dione were obtained. The melting point was 202° C with decomposition.

A further 5.1 g of product crystallised on evaporation of the dioxane filtrate. When these crystals were suction filtered, washed with dioxane and water, dried and treated with actone, they yielded a further 3.8 g of product. The combined crude products were dissolved in ether, filtered and precipitated with petroleum ether to yield 14.8 g (46.5% of the theory) of pure spiro-[1,3-benzodioxol-2,2'-imidazolidine]-4',5'-dione (compound 1), melting point 205° C with decomposition.

| Analysis: | C | H | N |
|---|---|---|---|
| Calculated: | 52.43 | 2.93 | 13.59 |
| Found: | 52.2 | 2.9 | 13.6 |

The following were prepared by a similar process: 5(6)-Chloro-spiro-[1,3-benzodioxol-2,2'-imidazolidine]-4', 5'-dione, m.p. 166° C with decomposition (Compound 4),5(6)-tert.-butyl-spiro-[1,3-benzodioxol-2,2'-imidazolidine]-4',5'-dione, m.p. 215° C with decomposition (Compound 5),5,6-dichloro-spiro-[1,3-benzodioxol-2,2'-imidazolidine]-4',5'-dione, melting point 190° C with decomposition (Compound 6), 5(6)-cyclohexyl-spiro-[1,3-benzodioxol-2,2'-imidazolidine]-4',5'-dione, m.p. 200° C with decomposition (Compound 10), 5(6)-tert.-octyl-spiro-[1,3-benzodioxol-2,2'-imidazolidine]-4',5'-dione, m.p. 226° C with decomposition (Compound 11) spiro-[1,3-benzoxathiolene-2,2'-imidazolidine]-4',5'-dione, m.p. 273° C with decomposition (Compound 9) by using o-thiophenol instead of pyrocatechol.

Example of Preparation 2

0.057 mol (7.25 g) of oxalyl chloride, dissolved in 250 ml of absolute dioxane, were added dropwise at 20° C to a solution of 0.057 mol (2.4 g) of anhydrous cyanamide in 570 ml of absolute dioxane. The mixture was stirred for 90 minutes and a solution of 0.171 mol (21.4 g) of o-aminothiophenol dissolved in 50 ml of absolute dioxane was slowly added. The mixture was then stirred for 2½ hours at 80° to 90° C. After cooling, the mixture was suction filtered to separate the resulting o-amino-thiophenol hydrochloride, and the filtrate was evaporated under reduced pressure. The evaporation residue was washed with water and dried. After recrystallisation from dimethylformamide, 3.3 g, which was 26.2% of the theoretical yield of spiro-[benzothiazoline-2,2'-imidazolidine]-4',5'-dione (Compound 2) were obtained. The melting point was 273° C with decomposition.

The yield was increased to 5.0 g which was 39.7% of the theoretical yield, by precipitating the dimethylformamide filtrate with ethanol.

| Analysis: | C | H | N | O | S |
|---|---|---|---|---|---|
| Calculated: | 48.86 | 3.19 | 18.99 | 14.46 | 14.49 |
| Found: | 50.25 | 3.47 | 19.2 | 14.3 | 14.4 |

The following was prepared in a similar manner: Spiro-[benzoxazoline-2,2'-imidazolidine]-4',5'-dione, m.p. 211°–212° C with decomposition (Compound 8), using o-aminophenol instead of o-amino-thiophenol.

Example of Preparation 3

0.302 mol (12.7 g) of anhydrous cyanamide were dissolved in 800 ml of anhydrous dioxane, and a solution of 0.302 mol (38.4 g) of oxalyl chloride in 400 ml of anhydrous dioxane was added dropwise over a period of 3 hours at 18° to 20° C. After 2 hours' stirring, 0.906 mol (98 g) of o-phenylene diamine dissolved in 400 ml of anhydrous dioxane was added dropwise. The mixture was then stirred at room temperature for 20 hours and the precipitated product was suction filtered, washed with dioxane and dried. To remove o-phenylene diamine-dihydrochloride, the crude product was stirred up with 1.7 liters of water for 1 hour, suction filtered, washed with water and dried.

5.3 which was 8.6% of the theoretical yield of pure spiro-[benzimidazoline-2,2'-imidazolidine]-4',5'-dione (Compound 3), m.p. 334°–336° C with decomposition, were obtained after recrystallisation from dimethylformamide.

| Analysis: | N |
|---|---|
| Calculated: | 17.3 |
| Found | 17.2 |

The following was prepared in a similar manner: 5(6)-Methyl-spiro-[benzimidazolidine-2,2'-imidazolidine]-4',5'-dione (Compound 7), m.p. 273° C with decomposition.

The compounds according to the invention are eminently suitable for use in the photographic materials described above. In contrast to the compounds known in the art, they cause no significant falsification of the color by formation of unwanted color oxidation products in the color photographic materials even if the materials are stored a long time.

The photographic materials according to the invention therefore consist in the simplest case of photographic materials suitable for the production of negative or reversed images containing transparent or opaque supports. The spiro compounds of the present invention can be added to at least one silver halide emulsion layer of the said material or to a colloidal intermediate layer positioned adjacent to a silver halide emulsion layer.

A preferred photographic material contains a hydrophobic support and in at least one silver halide emulsion layer or in at least one intermediate layer positioned adjacent to a silver halide emulsion layer the spiro compounds of the present invention.

A particular photographic material according to the present invention contains a substrate with a hydrophobic surface to which a hydrophilic colloid layer containing effective quantities of the heterocyclic spiro compounds is applied virtually immediately after the hydrophobic surface has been exposed to corona irradiation. This hydrophilic colloid layer may itself be a light-sensitive silver halide emulsion layer on a light-sensitive silver halide emulsion layer may be directly coated on the hydrophilic colloid layer which contains the heterocyclic spiro compound.

The hydrophilic colloid layer which contains silver halide emulsion preferably also contains a dispersion of color producing couplers which coupler with the oxidized color developer in the color development process to produce the desired color. One or more additional hydrophilic colloid layers containing differently sensitized light-sensitive silver halide emulsions either with or without dispersions of other color producing couplers are advantageously applied over the first silver halide emulsion layer.

A particular preferred photographic material according to the invention contains a polyolefine backed paper substrate which has been exposed to a corona discharge and which is coated successively with the following layers:

1. A hydrophilic colloid layer containing a blue sensitive silver halide emulsion and a dispersed yellow color coupler and the heterocyclic spiro compound according to the invention, 2. a hydrophilic colloid layer containing a green sensitized silver halide emulsion and a dispersed magenta coupler and 3. a hydrophilic colloid layer containing a red sensitized silver halide emulsion and a dispersed cyan color coupler.

The heterocyclic spiro compound is preferably contained in the dispersion which contains yellow coupler or in hydrophilic blue sensitive silver halide emulsion layer or it may be present in the dispersion and in the hydrophilic silver halide emulsion.

According to another preferred embodiment of the invention, the heterocyclic spiro compound is introduced into a hydrophilic colloid layer arranged between the electron irradiated polyolefine layer and the hydrophilic blue sensitive silver halide emulsion layer. Alternatively, the heterocyclic spiro compound may be introduced both into the hydrophilic colloid layer which is not light-sensitive and into the blue sensitive hydrophilic colloid layer as well as into the coupler dispersion of the blue sensitive colloid layer.

The variously sensitized silver halide emulsion layers containing dispersed color couplers may, of course, be placed in some other arrangement over the light-insensitive hydrophilic colloid layer which contains the spiro compound.

The compounds according to the invention may be used in color photographic materials which are suitable for recording purposes, copying purposes and as reversal materials.

The compounds according to the invention may be added to the photographic emulsion, the coupler dispersion or any auxiliary layers at any stage of their preparation and they may be used at various concentrations depending on the light-sensitive silver halide emulsions used in the individual case and the concentration of silver halide in the emulsion layers. It is generally sufficient to use a concentration of spiro compound of 0.1 to 15 g per mol of silver in the silver halide emulsion layer or 0.1 to 100 mg/m$^2$ in intermediate layers. In the silver halide emulsion layer applied to the hydrophobic support layer more or less immediately after exposure to the corona discharge, the spiro compound is preferably used in quantities of 0.2 to 4 g per mol of silver whereas if it is introduced into a hydrophilic colloid intermediate layer between the corona irradiated substrate and the first emulsion layer it is preferably used in quantities of 1 to 20 mg/m$^2$. The optimum concentration depends on the particular photographic recording material used, the nature of the emulsion, the sensitization of the emulsion, the kind and amount of color coupler and how they are dispersed in the emulsion. It can easily be determined by laboratory tests in the usual manner.

The spiro compounds are preferably added to the auxiliary layers and/or light-sensitive layer in the form of a solution. Suitable solvents for dissolving the spiro compounds include water, lower aliphatic alcohols, tetrahydrofuran, acetone, ethyl acetate, dimethylformamide and mixtures thereof. Another method of introducing the spiro compounds comprises preparing a common solution of the compounds according to the invention and color coupler so that the two are introduced together into the light-sensitive silver halide emulsion layer. Introduction of the compounds according to the invention into the light sensitive emulsion is preferably carried out after chemical ripening or before the finished emulsion is cast. If the compounds according to the invention are to be used in the light-insensitive layers, they are preferably added before casting.

According to the invention the supports used for the inventive materials include conventional hydrophilic supports such as paper and conventional hydrophobic supports, which can be treated by known means to improve the adhesion of hydrophilic photographic layers which are coated thereon.

The substrates with hydrophobic surfaces used according to the invention may be, for example, hydrophobic resinous foils which may be either self-supporting or applied to opaque or transparent support layers. The following are specific examples: Polyester films such as polyethylene terephthalate films, optionally electron irradiated, e.g. those described in U.S. Pat. No.

3,220,842, exposed to an electron beam so that they have a contact angle of less than 45° C; hardened gelatine layers optionally electron irradiated such as those described in U.S. Pat. No. 3,411,910; polyolefine surfaces which have been irradiated by the process described in the above mentioned British and U.S. Patents and which are preferably derived from olefines which contain 2 to 10 carbon atoms, e.g. polyethylene, polypropylene, poly(3-methylbutene-1), poly(octene-1), poly(decene-1) and polyamides, polyacetals, polycarbonates, esters and cellulose ethers, e.g. cellulose triacetate, cellulose acetate, cellulose butyrate and ethyl cellulose.

The substrates are preferably made of paper or some other fibrous material coated with a hydrophobic film surface made of the materials already described above. The hydrophobic layer, e.g. a polyolefine, is applied to the paper in the usual manner, for example by extruding a melt of the polyolefine or by applying the polyolefine from a solution, the paper substrate having preferably been first treated with an antistatic agent.

If treatment with corona discharge is wanted, this may be carried out by known methods such as those described in British Pat. Nos. 971,058 and 1,060,526, using apparatus described in U.S. Pat. Nos. 2,864,755 and 2,864,756.

According to the particularly preferred embodiment of the invention, at least one hydrophilic colloid layer which contains a light-sensitive silver halide and optionally also a color coupler is applied to a hydrophobic support immediately after irradiation. When the terms "directly", "immediately" or "substantially immediately" are used in this description, they denote a time interval of a few seconds, for example from 1 second to 30 minutes and preferably only a few seconds, e.g. not more than 1 second to 1 minute, which represents the time necessary to transport the substrate from the apparatus where the corona discharge takes place to the casting apparatus for the hydrophilic layer. It desired, the time interval that is allowed to elapse before the hydrophilic layer is applied may, of course, be extended to several hours, but it should be borne in mind that the strength with which it will adhere to the substrate then diminishes continuously with time.

The hydrophilic colloid used may be gelatine, which may be partly or completely replaced by other conventional natural or synthetic binders. Suitable natural binders include e.g. alginic acid and its derivatives such as salts, esters or amides, cellulose derivatives such as carboxymethylcellulose, alkyl cellulose such as hydroxyethyl cellulose, starch or its derivatives such as ethers or esters or carrageenates. Suitable synthetic binders include polyvinyl alcohol, partially saponified polyvinyl acetate, polyacrylamides and polyvinylpyrrolidone.

The usual silver halide emulsions are suitable for use in the materials according to the invention. The silver halides in them may be silver chloride, silver bromide or mixtures thereof, which may have a small silver iodide content of up to 10 mol %.

The emulsions may also be chemically sensitized, e.g. by adding sulphur compounds such as allyl isothiocyanate, allylthiourea or sodium thiosulphate at the stage of chemical ripening. Reducing agents may also be used as chemical sensitizers, for example the tin compounds described in Belgian Pat. Nos. 493,464 and 568,867 or polyamines such as diethylenetriamine or aminomethyl sulphinic acid derivatives, e.g. according to Belgian Pat. No. 547,323.

Noble metals and compounds of noble metals such as gold, platinum, palladium, iridium, ruthenium or rhodium may also be used as chemical sensitizers. This method of chemical sensitization has been described in the article by R. Koslowsky, Z.Wiss.Phot. 46, 65–72 (1951).

The emulsions may also be sensitized with polyalkylene oxide derivatives, e.g. with a polyethylene oxide having a molecular weight of between 1000 and 20,000, or with condensation products of alkylene oxides and aliphatic alcohols, glycols or cyclic dehydration products of hexitols or with alkyl substituted phenols, aliphatic carboxylic acids, aliphatic amines, aliphatic diamines or amides. The condensation products have a molecular weight of at least 700 and preferably more than 1000. These sensitizers may, of course, be combined to produce special effects as described in Belgian Pat. No. 537,278 and British Pat. No. 727,982.

The emulsions may also be optically sensitized, for example with the usual polymethine dyes such as neutrocyanines, basic or acid carboxyanines, rhodacyanines, hemicyanines, styryl dyes and oxonols. Sensitizers of this kind have been described in the work by F. M. Hamer "The Cyanine Dyes and Related Compounds" (Interscience Publishers).

The emulsions may contain known stabilizers, e.g. homopolar compounds or salts of mercury which contain aromatic or heterocyclic rings such as mercapto tetrazoles, simple mercury salts, sulphonium mercury double salts and other mercury compounds. Azaindenes, particularly tetra- or penta-azaindenes and especially those which are substituted with hydroxyl or amino groups are also suitable stabilizers. Compounds of this kind have been described in the article by Birr, Z.Wiss.Phot. 47, 2–58 (1952). Other suitable stabilizers include heterocyclic mercapto compounds, e.g. phenyl mercaptotetrazole, quaternary benzothiazole derivatives and benzotriazole and propynylthioether derivatives as described in German Offenlegungsschrift No. 2,304,321. The emulsions may be hardened in the usual manner, for example, with formaldehyde or halogenated aldehydes which contain a carboxyl group such as mucobromic acid, diketones, methanesulphonic acid esters and dialdehydes.

The photographic layers may also be hardened with epoxides, heterocyclic ethyleneimine compounds or acryloyl compounds. Examples of such hardeners have been described e.g. in German Offenlegungsschrift No. 2,263,602 and British Pat. No. 1,266,655. The layers may also be hardened by the process according to German Offenlegungsschrift No. 2,218,009 to obtain color photographic materials which are suitable for processing at high temperatures.

The photographic layers or color photographic multilayered materials may also be hardened with hardeners of the diazine, triazine or 1,2-dihydroquinoline series as described in British Pat. Nos. 1,193,290; 1,251,091; 1,306,544 and 1,266,655; French Pat. No. 7,102,716 and German Offenlegungsschrift No. 2,332,317. The following are examples of such hardeners: Diazine derivatives which contain alkyl or aryl sulphonyl groups, derivatives of hydrogenated diazines or triazines such as 1,3,5-hexahydrotriazine, fluoro-substituted diazine derivatives such as fluoropyrimidines, esters of 2-substituted 1,2-dihydroquinoline- or 1,2-dihydroisoquinoline-N-carboxylic acids. Vinyl sulphonic acid hardeners and carbodiimide or carbamoyl hardeners as described e.g. in German Offenlegungsschriften Nos. 2,263,602;

2,225,230 and 1,808,685; French Pat. No. 1,491,807; German Pat. No. 872,513 and DDR Pat. No. 7,218 may also be used. Other suitable hardeners have been described, for example, in British Pat. No. 1,268,550.

The emulsions may also contain other sensitivity increasing compounds, plasticizers and coating additives.

The materials according to the invention may contain color couplers, DIR couplers, masking and white couplers of various chemical compositions which may be introduced in a diffusion-fast form into hydrophilic binder layers, for example into a light-sensitive silver halide emulsion layer or into a light insensitive layer of binder adjacent thereto. The couplers are dispersed by known methods, e.g. with the aid of ethyl acetate and a wetting agent, and after removal of the auxiliary agent they are introduced into the emulsion in the form of a dispersion. If the coupler has a tendency to recrystallise in the dispersion, it is advisable to add an oil former, e.g. dibutylphthalate. Water-soluble couplers may also be used as well as couplers which are not diffusion-fast and which can be incorporated in the hydrophilic layers either with the aid of mordants or, in a classical photographic reversal process, with the aid of a color developer solution as described in U.S. Pat. No. 2,252,718. The cyan couplers used are compounds derived from phenol or α-naphthol, the magenta couplers are compounds derived from 2-pyrazolinone-5 compounds e.g. 3-acylamino- or 3-anilino-pyrazolino-5 compounds or from indazolone; the yellow couplers are compounds derived from β-ketocarboxylic acid derivatives, e.g. from pivaloylacetanilide or from benzoyl acetanilide. The couplers may be compounds which are not substituted in the coupling position or compounds which carry in the coupling position a substituent which is split off in the reaction with the developer oxidation product, for example 2-equivalent couplers or DIR couplers from which a splittable group or development inhibitor is liberated. Suitable color couplers have been described, for example, in the survey given in the article entitled "Farbkuppler" by W. Pelz in "Mitteilungen aus den Forschungslaboratorien de Agfa Leverkusen-Munchen", Volume 3, page 111 K. Venkatamaran, "The Chemistry of Synthetic Dyes", Vol. 4, pages 341–387, Academic Press 1971.

The DIR couplers used may be compounds which give rise to either colored or colorless products on liberation of a development inhibitor.

Masking couplers are generally colored color couplers from which an azo group is split off under the conditions of development, for example as described in U.S. Pat. No. 2,584,349.

The color materials according to the invention preferably contain the above mentioned color couplers as dispersions in the suitably sensitized silver halide emulsion layers. Color couplers which are alkali soluble are incorporated by dispersing the aqueous solution in the hydrophilic colloid phase in known manner while hydrophobic, diffusion-resistant couplers are incorporated by known dispersion methods such as those described, for example, in U.S. Pat. Nos. 2,322,027, 2,304,940, 2,801,171, 3,689,271, 3,764,336 and 3,765,897.

Suitable wetting agents which may be used according to the invention for incorporating photographic additives have been described by Gerhard Gewalek in "Wasch- und Netzmittel", Akademie-Verlag Berlin (1962). The following are examples: The sodium salt of N-methyl-oleyltauride, sodium stearate, the sodium salt of heptadecenylbenzimidazole sulphonic acid, sodium sulphonates of higher aliphatic alcohols, e.g. 2-methylhexanol sodium sulphonate, sodium diisooctyl sulphosuccinate, sodium dodecylsulphonate and the sodium salt of tetradecylbenzene sulphonic acid.

Color developers are used for producing the dye images in the photographic materials according to the invention, for example the usual aromatic compounds based on p-phenylene-diamine which contain at least one primary amino group. The following are examples of suitable color developers: N,N-Dimethyl-p-phenylenediamine; N,N-diethyl-p-phenylene-diamine; monomethyl-p-phenylenediamine; 2-amino-5-diethylamino-toluene; N-butyl-N-ω-sulphobutyl-p-phenylenediamine and 2-amino-5-(N-ethyl-N-β-methanesulphonamidoethylamino)-toluene. Other suitable color developers have been described, for example, in J.Amer.Chem.Soc. 73, 3000 to 3025 (1951).

EXAMPLE 1

30 g of an alkali soluble yellow coupler of the formula

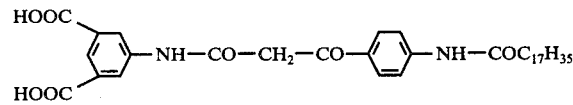

in aqueous methanolic sodium hydroxide solution were added to 1 kg of a silver iodobromide emulsion containing 0.24 mol of silver salt, consisting of silver bromide with a silver iodide content of 1 mol%. The pH of the emulsion was then adjusted to 6.4 and 1 g of saponin dissolved in water was added as wetting agent, 0.5 g of 4-hydroxy-6-methyl-1,2,3a, 7-tetraazaindene in aqueous alkaline solution was added as stabilizer and 1 g of triacryloformal in methanolic solution was added as hardener. The resulting emulsion was divided into 10 equal parts and the compounds according to the invention shown in the following table were added in the quantities indicated to the individual samples.

Table 1

| Sample | Compound | g/mol Ag | $D_{min}$ |
|---|---|---|---|
| 1 a | no additive | — | 0.34 |
| 1 b | no additive | — | 0.06 |
| 2 | 1 | 2 | 0.07 |
| 3 | 2 | 2 | 0.12 |
| 4 | 4 | 2 | 0.10 |
| 5 | 5 | 2 | 0.07 |
| 6 | 6 | 2 | 0.07 |
| 7 | 10 | 2 | 0.07 |
| 8 | 11 | 2 | 0.06 |
| 9 | hydroquinone | 2 | 0.07 |
| 10 | phenidone | 2 | 0.15 |

Emulsion sample 1 was divided into two portions and sample 1 a as well as emulsion samples 2 to 10 were cast on corona irradiated polyethylene coated paper in amounts corresponding to a silver application of 5 ml of silver halide per m². The emulsions were applied 10 seconds after the polyethylene coated paper substrate had been exposed to the corona discharge current as described in U.S. Pat. No. 2,864,756, column 4. Emulsion sample 1 b was applied to a polyethylene coated paper substrate which had been stored for 24 hours after the corona irradiation described above. A 2% gelatine solution was applied in a thickness corresponding to 2 g of gelatine per m² as protective layer to each emulsion layer.

After drying, the materials are developed without exposure in a developer of the following composition for 5 minutes at 20° C:

5 g of N-butyl-N-ω-sulphobutyl-p-phenylenediamine,
1.2 g of hydroxylamine hydrochloride,
2 g of sodium sulphite sicc.
2 g of sodium metaphosphate,
75 g of potassium carbonate,
1 g of potassium bromide,
made up with water to 1 liter.

The subsequent treatment includes the following baths:

Short stop bath: a buffer solution of sodium acetate and acetic acid adjusted to pH 6.5.

Bleach fix bath:
10 g of the sodium salt of ethylenediaminotetracetic acid,
2 g of the sodium sulphite sicc.,
40 g of the sodium-iron-(III) salt of ethylenediaminotetracetic acid,
13 g of disodium phosphate,
100 g of ammonium thiosulphate,
made up to 1 liter with water and adjusted to pH 7.0.

The processing times after development are as follows:
1 minute short stop bath,
1 minute washing,
5 minutes bleach fix bath,
10 minutes washing.

The minimum densities obtained in the individual samples are shown in the above table 1. On comparing sample 1 b with sample 1 a, it can be clearly seen that the minimum density is considerably increased by immediate application to a corona irradiated substrate. Samples 9 and 10 are comparison samples containing the most effective reducing agents from U.S. Pat. No. 3,582,333. Yellowing is found to occur in the unprocessed sample 9 if it is stored before exposure but is found to be substantially absent in materials 3 to 8 according to the invention which have been stored. The prior art reducing agent used to prevent fogging, for example the one in sample 9, competes with the color couplers in the material to couple with the oxidized color developer which results in an unwanted dirty green dye.

EXAMPLE 2

Example 1 was repeated except that instead of the alkali soluble yellow coupler, a coupler of the following structure was used.

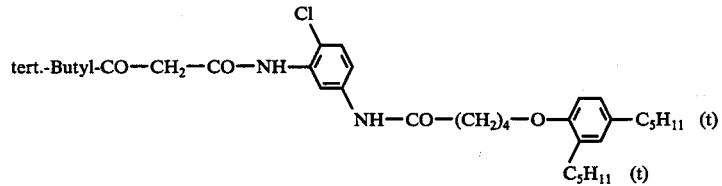

which was added to the emulsion by Example 1 by the following method:

Preparation of the coupler dispersion 10 g of color coupler are dissolved in 10 g of dibutyl phthalate, 20 g of butyl acetate and 2 g of dodecylbenzene sulphonic acid sodium and emulsified in 300 g of a 10% gelatine solution at 40° C, using a mixing siren. The solvent is removed from the emulsion by distillation in a thin layer evaporator.

The resulting coupler dispersions were added to samples of emulsions in quantities corresponding to 40 g of coupler per mol of silver halide. Stabilizers, wetting agents and hardeners were then added to the emulsion samples as described in Example 1.

The results shown in Table 2 below were obtained as described in Example 1.

Table 2

| Sample | Compound | g/mol of Ag | $D_{min}$ |
| --- | --- | --- | --- |
| 1 a | no additive | — | 0.34 |
| 1 b | no additive | — | 0.07 |
| 2 | 1 | 2 | 0.07 |
| 3 | 2 | 2 | 0.11 |
| 4 | 4 | 2 | 0.09 |
| 5 | 5 | 2 | 0.08 |
| 6 | 6 | 2 | 0.08 |
| 7 | 10 | 2 | 0.08 |
| 8 | 11 | 2 | 0.07 |
| 9 | hydroquinone | 2 | 0.08 |
| 10 | phenidone | 2 | 0.17 |

EXAMPLE 3

Example 2 was repeated except that a panchromatically sensitized emulsion containing a cyan coupler of the following formula was used instead of the blue sensitive emulsion with yellow coupler used in Example 2:

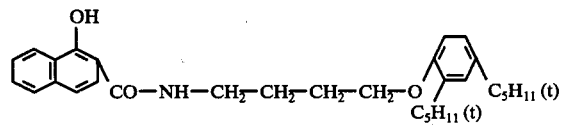

When these samples are developed, no increase in minium densities is found in any of the experiments. In those samples which are exposed before development in a conventional sensitometer in such a way that approximately a uniform medium density is developed in the developer it is found that a coarse cloudiness is produced in sample 1 a. This cloudiness is due to the fact that the reaction products produced by corona irradiation vary in concentration over the surface of the irradiated support and cause localized differences in sensitivity loss in the light-sensitive emulsion. Sample 1 b, in which the irradiated substrate was stored for 24 hours between the corona discharge treatment and casting, is free from cloudiness like the emulsion samples which contain the compounds according to the invention, and it has a homogeneous constant image density. The results are summarized in Table 3.

Table 3

| Sample | Compound | g/mol of Ag | Valuation of medium density of the image |
| --- | --- | --- | --- |
| 1 a | no additive | — | heavy cloudiness |
| 1 b | no additive | — | constant density |
| 2 | 1 | 2 | constant density |
| 3 | 2 | 2 | constant density |
| 4 | 4 | 2 | constant density |

Table 3-continued

| Sample | Compound | g/mol of Ag | Valuation of medium density of the image |
| --- | --- | --- | --- |
| 5 | 5 | 2 | constant density |
| 6 | 6 | 2 | constant density |
| 7 | 10 | 2 | constant density |
| 8 | 11 | 2 | constant density |
| 9 | hydroquine | 2 | constant density |
| 10 | hydroquinone | 0.10 | constant density |
| 11 | phenidone | 0.6 | constant density |

There is no change in gradation in the emulsions containing the compounds according to the invention whereas, in the emulsions containing prior art compounds, particularly in samples 9 and 10, a loss of threshold sensitivity of about 1.5° DIN is observed.

EXAMPLE 4

Example 1 was repeated but a pigmented polyethylene terephthalate substrate was used instead of the substrate described in Example 1 and the quantity of additives was changed as shown below. The surface was treated as described in Example 1 British Pat. No. 971,058.

Table 4

| Sample | Compound | g/mol of Ag | $D_{min}$ |
| --- | --- | --- | --- |
| 1 a | no additive | — | 0.28 |
| 1 b | no additive | — | 0.08 |
| 2 | 1 | 0.50 | 0.08 |
| 3 | 2 | 0.50 | 0.10 |
| 4 | 4 | 0.50 | 0.09 |
| 5 | 5 | 0.50 | 0.08 |
| 6 | 6 | 0.50 | 0.07 |
| 7 | 10 | 0.50 | 0.06 |
| 8 | 11 | 0.50 | 0.07 |
| 9 | hydroquinone | 0.50 | 0.07 |
| 10 | phenidone | 0.50 | 0.13 |

EXAMPLE 5

Examples 1 to 4 were repeated except that the blue sensitive emulsion layer was applied to each substrate 30 seconds and 20 minutes after the corona surface treatment.

The results obtained clearly show that the formation of basic fog (higher $D_{min}$ value) is progressively reduced the longer the period of time which elapses between irradiation and application of the light-sensitive layer. The results also show that the compounds according to the invention, as indicated in Examples 1 to 4, are still superior to the prior art compounds after 20 minutes.

EXAMPLE 6

A. Preparation of Comparison Samples

On a corona irradiated polyethylene coated paper support was cast 24 hours after the exposure of the support to the corona discharger the following layers one onto the other:

1. a photographic blue sensitive silver bromide containing emulsion containing per liter 35 g of gelatin, 0.1 mol of silver halide and 15 g of a yellow coupler (to provide 1.6 g of gelatin per m²).
2. a gelatine intermediate layer to provide 1.0 g gelatine per m² (to improve color separation in the material).
3. a green sensitized silver-chloride bromide emulsion containing a magenta coupler (to provide 0.05 mol silver halide, 1.5 g gelatin and 0.4 g of magenta coupler per m²).
4. a gelatine intermediate layer to provide 1.0 g gelatine per m².
5. a red sensitized silver chloride bromide emulsion containing a cyan coupler (to provide 0.035 mol silver halide, 1.1 g gelatin and 0.2 g of cyan coupler per m²).
6. a gelatine protective layer of 1 μ thickness (to provide the photographic material a protection against mechanical deleterious influences.

The photographic material was exposed behind a step wedge divided into samples and processed. The development of the samples was carried out at 25° C and one sample being developed for 4 minutes the other sample being developed for 8 minutes in a color developer of the following composition:

4 g of N-butyl-N-ω-sulphobutyl-p-phenylenediamine
2 g of sodium hexametaphosphate
60 g of potassium carbonate
3 g of sodium sulfite
0.3 g of potassium bromide
2 g of hydroxylamine hydrochloride and water up to 1 l.

The subsequent treatment includes the following baths: short stop bath, 3 minutes bleach-fix bath and a washing bath for 5 minutes in running water. (The composition of stop bath and bleach-fix bath according to Example 1).

The couplers used in the material had the following formulae:

Yellow coupler:

$$CH_3-O-\underset{SO_3H}{\underset{|}{\phantom{X}}}\text{-}CO-CH_2-CO-NH-\underset{OC_{16}H_{33}}{\underset{|}{\phantom{X}}}\text{-}SO_2NHCH_3$$

Magenta coupler:

(structure with tert. $C_4H_9$, $O-CH_2-CH_2-O-CO-NH$, Cl substituents, and pyrazolone ring with trichlorophenyl)

Cyan coupler:

(structure: OH, Cl, $CH_3$, Cl substituted phenol with $-NH-CO-CH(CH_3)-O-$ linked to tert.-$C_4H_9$ cyclobutyl phenyl)

B. Preparation of Samples according to the invention

The inventive photographic material was prepared as the comparison material A with the exception that the intermediate layer 2 contains 20 mg of compound 13 per g of gelatin.

Exposure and processing of the inventive Samples were performed as described in connection with the comparison samples.

The sensitometric results of the inventive Samples (B) and comparison samples (A) are summarized in the following Table 5.

Table 5

| Sample | Development Time | Yellow | Magenta | Cyan | |
|---|---|---|---|---|---|
| B | 4 | 1.15 | 1.35 | 1.42 | Sensitivity |
|   |   | 2.50 | 2.25 | 2.20 | Gradation |
|   |   | 0.11 | 0.10 | 0.11 | Fog |
| B | 8 | 0.98 | 1.23 | 1.35 | Sensitivity |
|   |   | 2.68 | 2.30 | 2.30 | Gradation |
|   |   | 0.15 | 0.14 | 0.14 | Fog |
| A | 4 | 1.10 | 1.30 | 1.40 | Sensitivity |
|   |   | 2.40 | 2.2 | 2.1 | Gradation |
|   |   | 0.14 | 0.12 | 0.11 | Fog |
| A | 8 | 0.95 | 1.20 | 1.30 | Sensitivity |
|   |   | 2.6 | 2.3 | 2.25 | Gradation |
|   |   | 0.2 | 0.18 | 0.14 | Fog |

By comparing the fog values the addition of the spiro compound of the present invention to the interlayer significantly reduces the fogging degree.

Moreover it could be noticed that the addition of the spiro compound of the present invention in the intermediate layer improves the separation of the yellow and magenta colors. Unwanted coupling of yellow coupler with oxidized color developer substances which were produced in the green sensitized layers and could diffuse into the blue sensitive layer could be remarkably reduced. And as well the unwanted coupling of magenta coupler with oxidized color developer substances which were produced in the blue sensitive layer and could diffuse into the green sensitive layer was equally reduced.

EXAMPLE 7

A photographic material was prepared as described in Example 6A with the exception that 1 g of spiro compound 12 (spiro derivative of 2,3-dihydroxy-naphthaline) was added prior to the casting to the green sensitized silver halide emulsion.

After exposure and development which was carried out as described in Example 6 the following sensitometric results were obtained.

Table 6

| Development Time (minutes) | Yellow | Magenta | Cyan | |
|---|---|---|---|---|
| 4 | 1.12 | 1.28 | 1.40 | Sensitivity |
|   | 2.42 | 2.22 | 2.12 | Gradation |
|   | 0.13 | 0.10 | 0.10 | Fog |
| 8 | 0.95 | 1.20 | 1.31 | Sensitivity |
|   | 2.55 | 2.31 | 2.20 | Gradation |
|   | 0.18 | 0.14 | 0.13 | Fog |

The above test shows that in the inventive material the fogging degree is advantageously reduced if compared to the corresponding values obtained with comparison samples A of Example 6 without significantly impairing the other sensitometric values in the inventive material.

We claim:

1. In a photographic material containing at least one silver halide emulsion layer and a support and a stabilizer compound the improvement according to which the stabilizer compound is a phenyl compound in which the phenyl ring is ortho disubstituted with oxygen, sulfur or —NH— as bridging members being linked together to form a spiro structure with 2'-imidazolidine-4',5'-dione.

2. Photographic material according to claim 1 in which the stabilizer compound is a compound of the following structural formula

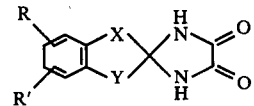

in which R and R' which may be the same or different, represent hydrogen, alkyl with 1 to 10 carbon atoms, phenyl, phenylalkyl, the alkyl group having up to 4 carbon atoms, cycloalkyl or halogen or R and R' may together represent the carbon atoms required to close a condensed cyclohexene, cyclohexadiene or benzene ring, X represents oxygen or -NH- and Y represents oxygen, sulfur or —NH—.

3. Photographic material as claimed in claim 1 in which the support is hydrophobic.

4. Photographic material as claimed in claim 3 in which the support is an electron irradiation or corona discharge treated hydrophobic support.

5. In a process for the production of color photographic materials by treatment of the surface of a hydrophobic support with an electron beam or corona discharge to improve the adhesion of the support to hydrophilic colloid layers, at least one silver halide emulsion layer being applied onto the support, which layers are applied onto the support after said electron beam or corona discharge treatment, the improvement according to which at least one of said layers is provided with a phenyl compound in which the phenyl ring is ortho disubstituted with oxygen, sulfur or —NH— as bridging members being linked together to form a spiro structure with 2'-imidazolidine-4',5'-dione.

6. The process of claim 5 in which the silver halide emulsion layer is applied to the treated support within a period of from one second to several hours after the surface treatment.

7. In the process for the production of color photographic materials by electron beam or corona discharge treatment of the surface of a hydrophobic support as claimed in claim 5 after said treatment of said surface first applying an intermediate layer between the support and the silver halide emulsion layer, said phenyl compound being included in said intermediate layer.

* * * * *